US008099156B1

(12) United States Patent
Schnitzer et al.

(10) Patent No.: US 8,099,156 B1
(45) Date of Patent: Jan. 17, 2012

(54) COCHLEAR OPTICAL ANALYSIS SYSTEM AND APPROACH THEREFOR

(75) Inventors: Mark Jacob Schnitzer, Stanford, CA (US); Nikolas H. Blevins, Portola Valley, CA (US); Eunice Lap Mun Cheung, Potsdam, NY (US); Juergen Claus Jung, Palo Alto, CA (US); Ashkan Monfared, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1147 days.

(21) Appl. No.: 11/855,606

(22) Filed: Sep. 14, 2007

Related U.S. Application Data

(60) Provisional application No. 60/844,856, filed on Sep. 15, 2006.

(51) Int. Cl.
*A61B 6/00* (2006.01)
(52) U.S. Cl. ........................ 600/476; 600/478
(58) Field of Classification Search .................. 600/473, 600/476, 477, 478, 407
See application file for complete search history.

(56) References Cited

U.S. PATENT DOCUMENTS

| | | | |
|---|---|---|---|
| 5,419,312 A | 5/1995 | Arenberg et al. | |
| 5,929,985 A | 7/1999 | Sandison et al. | |
| 6,571,118 B1 | 5/2003 | Utzinger et al. | |
| 6,639,674 B2 | 10/2003 | Sokolov et al. | |
| 6,640,121 B1 * | 10/2003 | Telischi et al. | 600/379 |
| 6,766,184 B2 | 7/2004 | Utzinger et al. | |
| 6,979,553 B2 * | 12/2005 | Farinas et al. | 435/29 |
| 2003/0103262 A1 | 6/2003 | Descour et al. | |
| 2005/0157981 A1 | 7/2005 | Berier et al. | |
| 2005/0207668 A1 | 9/2005 | Perchant et al. | |
| 2005/0242298 A1 | 11/2005 | Genet et al. | |

OTHER PUBLICATIONS

A Monafared, NH Blevins, ELM Cheung, JC Jung, G Popelka, MJ Schnitzer. In Vivo Imaging of Mammalian Cochlear Blood Flow Using Fluorescence Microendoscopy. Otol Neurotol. 2006; 27(2): 144-151.*
HH Nakajima, DC Mountain, AE Hubbard. Nonlinear Characteristics of Electrically Evoked Otoacoustic Emissions. Hearing Research. 1998; 122(1-2): 109-118.*

* cited by examiner

*Primary Examiner* — Brian Casler
*Assistant Examiner* — Amanda Lauritzen
(74) *Attorney, Agent, or Firm* — Crawford Maunu PLLC (57) ABSTRACT

A micro-optical probe approach facilitates imaging, testing and/or analysis of cochlear tissue. According to an example embodiment, a probe is implanted into cochlear tissue of a live being and used to obtain an image of cochlear tissue and the image is used to characterize a condition of auditory function of the cochlear tissue as represented, for example, by fluid flow in the tissue. Certain embodiments are directed to the use of a fluorescent dye to label cochlear tissue. A fluorescent response of the dye to stimulation is detected and used to characterize the cochlear tissue. In some applications, the probe is used to guide the implant of a cochlear prosthesis.

28 Claims, 6 Drawing Sheets

FIG.6B

COCHLEAR OPTICAL ANALYSIS SYSTEM AND APPROACH THEREFOR

RELATED PATENT DOCUMENTS

This patent document claims the benefit, under 35 U.S.C. §119(e), of U.S. Provisional Patent Application No. 60/844,856 filed on Sep. 15, 2006 and entitled: "Cochlear Optical Analysis System and Approach Therefor," which is fully incorporated herein by reference.

FIELD OF THE INVENTION

The present invention relates generally to optical analysis, and more particularly to analysis approaches involving the optical analysis of cochlear tissue.

BACKGROUND

A variety of approaches to optical imaging and analysis have been used for many different applications. For example, the endoscope is a useful tool for a variety of applications such as biological research, medical diagnostics, and for image guidance in surgical procedures. Conventional endoscopes utilize a white light source to illuminate a sample and reflected light to visualize the same sample. Such conventional endoscopes are typically limited, however, to visualizing the surface of a sample or to surface inspection within a hollow tissue cavity.

Many applications for which optical analysis would be beneficial are subject to a variety of limitations. For example, space constraints in many applications limit the use of certain tools or approaches that are not generally scaleable in a manner that would facilitate use with these applications. In addition, while certain approaches have been useful in applications characterized by small space constraints, these approaches are often limited in their ability to achieve desirable results, or by their ability for use with certain applications such as with the analysis of tissue in live beings.

One type of tissue that has been particularly difficult to access for examination and surgical intervention is cochlear tissue in the inner ear. In particular, visualization of structures inside the inner ear in vivo has been limited by their small size and inaccessible location deep in the temporal bone.

Analysis of cochlear tissue is important; it has been estimated that 50% of adults living in industrialized countries will suffer some permanent hearing loss by 75 years of age. For instance, hearing loss related to inner ear disorders is a widespread problem that impacts about 28 million Americans. Yet, otologists have been severely limited in their ability to diagnose even common pathology, let alone to treat disease in a non-destructive manner For patients with sudden hearing loss or acute vertigo, otologists are usually forced to list numerous potential causes before admitting the cause is unknown. Treatment is thus compromised, since the various potential causes of hearing loss may respond quite differently to specific interventions.

Much hearing loss is thought to stem from damage to the sensory receptor cells in the cochlea. These hair cells are found in a tonotopically organized ribbon 4-5 cells wide and about 5,000 cells long that coils along the length of the cochlea, with higher frequencies at the basal end and lower frequencies at the apical end. Sound vibrates the basilar membrane on which the hair cells ride, and causes a relative shearing between the apical surfaces of the cells and a membrane contacting the tops of their mechanosensory bundles. This mechanical stimulation directly opens ion channels found at the tips of the stereocilia that constitute the bundle.

Previous approaches to assessing damage to the cochlea has been assessed either indirectly in vivo using electrical methods to monitor the auditory nerve firings or the auditory brainstem response (ABR), or more directly in vitro by excising sections of the cochlea and studying the anatomy. However, these approaches have been limited in resolution and, for the latter approach, are not possible for use with treating live beings.

The above and other issues have presented challenges to optical analysis approaches and, in particular, to optical imaging in applications exhibiting relatively small space such as for endoscopic and microscopic applications.

SUMMARY

The present invention is directed to overcoming the above-mentioned challenges and others related to the types of devices and applications discussed above and in other applications. These and other aspects of the present invention are exemplified in a number of illustrated implementations and applications, some of which are shown in the figures and characterized in the claims section that follows.

According to an example embodiment of the present invention, cochlear tissue of a live being is imaged in-vivo. A lower distal end of a micro-optical probe is inserted into cochlear tissue of the live being. Light is directed to the cochlear tissue via the micro-optical probe. Light from the cochlear tissue is passed, via the micro-optical probe, to an external imaging arrangement. The light passed from the cochlear tissue is used at the external imaging arrangement to optically image fluid of the live being in a field of view, with the micro-optical probe inserted into the cochlear tissue. With this approach, a condition of functionality of sensory receptor cells of the cochlear tissue is indicated.

According to another example embodiment of the present invention, cochlear tissue of a live being is imaged in-vivo using a fluorescent dye. A fluorescent dye is introduced to the blood of a live being to label blood cells with the dye. A lower distal end of a micro-optical probe is inserted into cochlear tissue of the live being, and light is directed to blood in the cochlear tissue via the micro-optical probe to cause fluorescent emissions from blood cells labeled with the fluorescent dye. The fluorescent emissions are passed from the cochlear tissue, via the micro-optical probe, to an external imaging arrangement. At the external imaging arrangement, the fluorescent emissions are used to obtain images of individual blood cells that characterize blood flow in the cochlear tissue of the live being, and in some applications, the blood flow in individual blood vessels. The imaged blood flow is used to determine a condition of auditory function of the cochlear tissue.

According to another example embodiment of the present invention, an arrangement for in-vivo viewing of cochlear tissue of a live being includes a micro-optical probe and an external imaging arrangement. The micro-optical probe is adapted for insertion into cochlear tissue of the live being, to direct light to the cochlear tissue and to pass light from the cochlear tissue to the external imaging arrangement. The external imaging arrangement is adapted to use the light passed from the cochlear tissue to optically image fluid of the live being in a field of view with the micro-optical probe inserted into the cochlear tissue, and thereby indicate a condition of functionality of sensory receptor cells of the cochlear tissue.

The above overview is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and approaches, and the invention has been found to be particularly suited for approaches to optical in-vivo cochlear tissue analysis. While the present invention is not necessarily limited to such applications, various aspects of the invention may be appreciated through a discussion of various examples using this context.

According to an example embodiment of the present invention, a microendoscope is inserted into cochlear tissue of a live being and the tissue is imaged via fluorescence microendoscopy. The microendoscope is used to image characteristics such as the arrangement and/or composition of the tissue, blood flow in the tissue (or the ability of blood to flow in the tissue), or other characteristics that may be related to hearing functions. For various embodiments, the images are used to analyze characteristics of the live being's cochlear tissue for several applications, including disease analysis, repair and prosthetic applications.

According to another example embodiment of the present invention, the basal turn of cochlea are imaged using microendoscopes through a small cochleostomy (an opening of the perilymphatic spaces of the cochlea). Using an intravenous dye injection (e.g., fluorescein) and a microendoscope that employs gradient refractive index (GRIN) micro-lenses (e.g., 350-1000 microns in diameter), the flow of individual red blood cells within capillaries in the inner ear are visualized in live beings. With this approach, the blood flow in individual blood vessels can be detected.

In some embodiments, images are captured and used to characterize the velocity of fluid flow, such as the velocity of blood cells, to characterize the flow of blood within the capillaries. For example, by inserting a microendoscope probe as discussed above into cochlear tissue (e.g., in a human or other mammalian subject), a series of images can be captured by way of the probe using, for instance, one-photon microscopy, discussed further below. In certain applications, a fluorescent substance, such as a dye that marks red blood cells, is introduced into the live being to facilitate the imaging of fluid flow.

Other embodiments are directed to the detection of the presence of a marker such as a dye that is carried by blood. The marker is injected into the blood stream of a subject and, at a later time, cochlear tissue is analyzed using a microendoscope to detect the presence of the marker. If the marker is present in the cochlear tissue, its presence can be used as an indicator of blood flow to the tissue. Correspondingly, the absence of the marker is an indicator of the inability of blood to flow to the tissue. This approach is useful, for example, for identifying transduction channels that are malfunctioning (e.g., due to damage) and, thereby identifying damaged cochlear tissue. The same tissue can be monitored for the presence of the marker over time, with subsequent detection of the marker used to identify recovery of the damaged tissue. In addition, where damage is to be corrected, the identification of damaged cochlear tissue can be used to facilitate the implantation of a cochlear prosthetic device to mitigate the damage (e.g., to restore lost hearing).

In connection with various example embodiments herein, images of cochlear tissue are captured in a manner that does not substantially affect the auditory operation of the cochlear tissue and/or surrounding tissue (e.g., such that the probe affects a subject's hearing insubstantially and/or not at all, facilitating in-vivo imaging of live beings). For instance, in some applications, these approaches facilitate the insertion of a probe while generally preserving sensitive and surrounding anatomical structures, such as the facial nerve and blood supply to cochlear and other tissue (e.g., thus insubstantially affecting surrounding tissue).

In another example embodiment, a damaged or diseased ear is imaged using a fluorescence microendoscopy (FME) arrangement. Often, when an ear becomes damaged or diseased, cochlear nerve fibers that relay signals to the brain are damaged. These cochlear nerve fibers are imaged using the FME arrangement to characterize (e.g., map) the number, spatial distribution and/or characteristics of cochlear nerve fibers. The images are then used in analyzing the cochlear tissue for one or more of a variety of purposes.

In some embodiments, images obtained with an FME approach as discussed above are used to identify dysfunctional tissue. The identified tissue is then used to identify an approach to the implantation of a cochlear prosthesis (e.g., to determine the location and/or type of implant) to facilitate hearing. In certain implementations, an FME arrangement is further used to guide the placement of a prosthesis device.

In another embodiment, this FME approach is used to map viable cochlear nerve fibers that remain available to relay signals to the patient's brain. Such mapping is facilitated intraoperatively, prior to a surgical procedure, to non-destructively map neurons that project these fibers. In some applications, the FME approach is used to map viable nerve fibers in preparation for a cochlear implant. The identified viable cochlear nerve fibers are used to select the position and orientation of the implant, and the implant is inserted relative to the selected position and orientation.

In some implementations, maps of the location, density, and electrical sensitivity of cochlear neurons and the proximal portions of the nerve fibers are created using both anatomic appearance (e.g., as visualized via an FME-obtained image) and neuronal activity assessed optically via the FME for assessing performance of a cochlear implant. This information is used, for example, in assessing a patient's post-implantation hearing performance. These assessments are used for a variety of purposes, such as in the design of more effective implants, to characterize an arrangement of implant electrodes to stimulate neurons that remain active, or to customize the electrical characteristics of an implant to better suit a particular individual's inner ear structure and function.

In various embodiments, such as described in connection with the preceding paragraph, cochlear tissue is electrically stimulated to generate cochlear neural activity in a manner that mimics, at least in part, the nonlinear mechanisms of cochlear transduction. An FME approach as described herein is used to image the cochlear tissue to optically detect characteristics of the cochlear tissue and facilitate the observation of the behavior of the cochlear tissue.

In connection with other example embodiments of the present invention, a micro-optical probe is implemented to image cochlear tissue of a live being to facilitate the manipulation of the cochlear tissue. For example, one embodiment is directed to the use of a laser to remove pathologic adhesions or fibrosis, ablate a portion of a dysfunctional stria vascularis in cases of endolymphatic hydrops, or manipulate the vibratory characteristics of the basilar membrane to enhance its vibratory resonance. The approaches described herein involve imaging with a micro-optical probe to facilitate the ability to see the microanatomy of the inner ear, and the subsequent improvement of the function of the inner ear through micromanipulation.

According to another example embodiment of the present invention, a cochlear analysis arrangement includes an implantable capillary-type device that facilitates acute (single) and/or iterative in vivo access to cochlear tissue of a specimen via an externally-applied probe, such as described above. The capillary-type device is adapted for insertion at cochlear tissue, and to remain implanted in the cochlear tissue for subsequent analysis. A closed end of the capillary is implanted in a patient (i.e., subcutaneously), with an open end of the capillary accessible for insertion of an optical probe. The lower end of the capillary is implanted adjacent a target area of the cochlear tissue to be imaged, and is adapted to pass light between the inserted probe and the target area.

In view of the above discussion as well as that described in connection with the figures below, various embodiments are directed to the use of fluorescence microendoscopy to characterize a condition of cochlear tissue, determine a prosthetic solution to hearing recovery in patients exhibiting damaged cochlear tissue, and guiding the implant of prosthesis in accordance with such a prosthetic solution. Similarly, various embodiments are directed to the analysis of hearing loss in live beings, to facilitate an understanding of the behavior of cochlear tissue in relation to hearing loss and both natural and prosthetic hearing recovery. Still other embodiments are directed to the detection of damaged or dysfunctional cochlear tissue, and to further guide the manipulation and/or removal of cochlear tissue to address the damage or dysfunction.

Certain embodiments are directed to the imaging of cochlear tissue over time to facilitate the various approaches to the analysis of cochlear tissue and/or corrective actions taken therewith as described herein. Some implementations involve the use of an implanted capillary that facilitates: the placement of an FME probe to image cochlear tissue; the removal of the probe; and the subsequent replacement of the probe at a later time to further image the cochlear tissue. The capillary can be left implanted in a live being, which can be allowed to move freely (e.g., between FME imaging sessions). Example approaches involving a capillary are described further below, in connection with FIG. 5 and as otherwise applicable.

Figure 1:
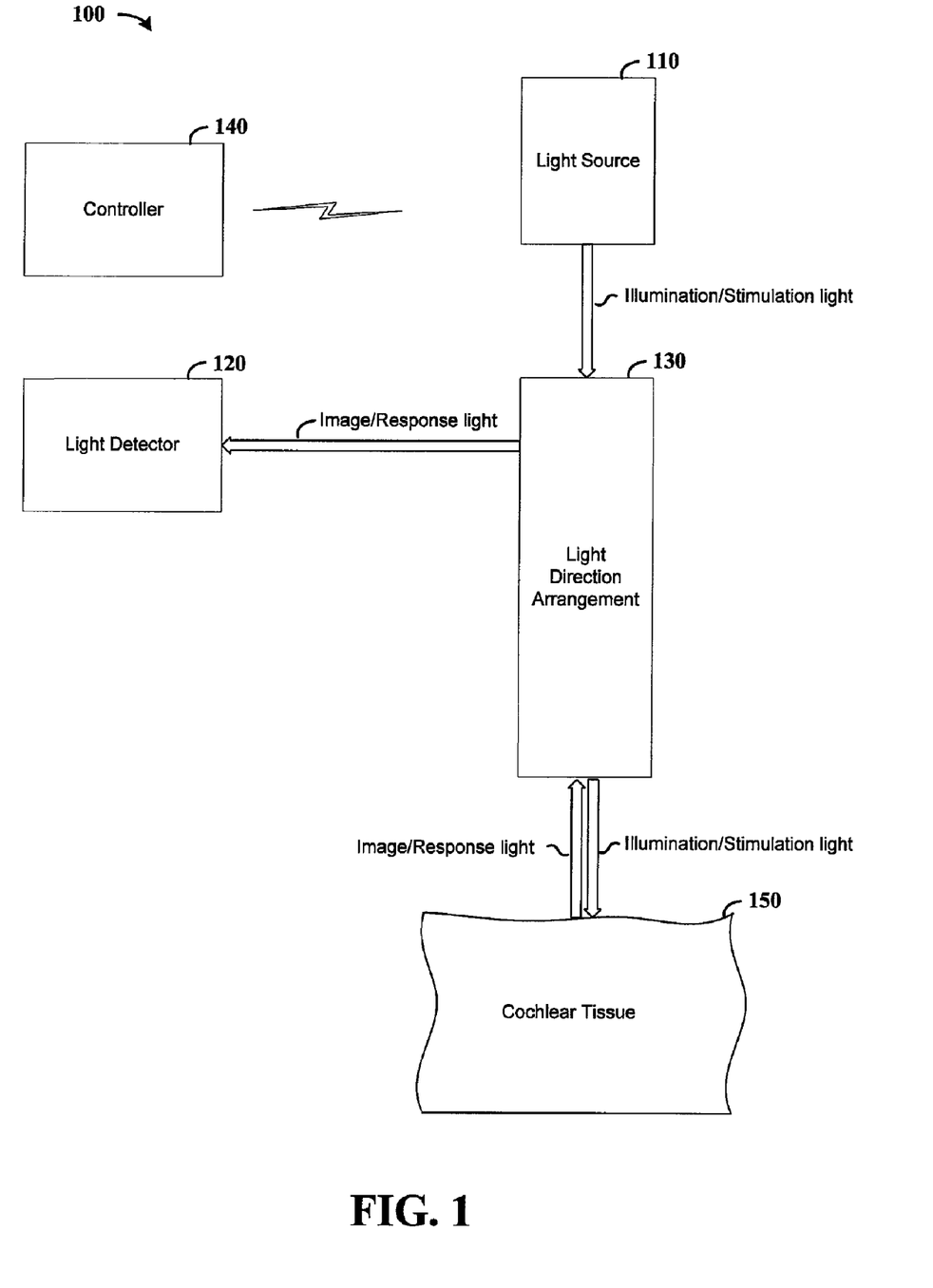
FIG. 1 shows a system for optical imaging, according to an example embodiment of the present invention.

Turning now to the figures, FIG. 1 shows an optical analysis system 100 for analyzing cochlear tissue 150, according to another example embodiment of the present invention. The optical analysis system 100 includes a light source 110 that passes light (e.g., for illumination and/or stimulation) through a light-direction arrangement 130 to the cochlear tissue 150, and that passes light characterizing the cochlear tissue to a detection arrangement 120. The light passed to the detection arrangement 120 includes, for example, an emission from a fluorescent dye in the cochlear tissue 150 that can be used to characterize a condition of the cochlear tissue as described above, or light generated in response to an optical, chemical or electrical stimulus.

The light-direction arrangement 130 includes a dichroic device, such as a beam splitter, to facilitate the passage of light to and from the cochlear tissue 150. In some applications, the light-direction arrangement 130 also includes a micro-mirror arrangement that is controlled via a controller 140 to direct the light to specific locations in the cochlear tissue 150. In one implementation, the dichroic device is arranged between the micro-mirror arrangement and the cochlear tissue 150; in another implementation, the micro-mirror arrangement is arranged between the dichroic device and the cochlear tissue 150. While shown separately, the controller 140 is included with the light-direction arrangement 130 for certain applications. In addition, the controller 140 may be implemented using, for example, a computer processor programmed to supply a control output and, where appropriate, other devices to appropriately use the control output to control the direction of light to the cochlear tissue 150.

The light direction arrangement 130 directs (and in some applications, scans) the stimulation light to a target portion of the cochlear tissue 150 of a living being. Light from the cochlear tissue 150 is passed through the light direction arrangement 130 and to the light detection arrangement 120. In some applications, the light direction arrangement 130 implements a wavelength-dependent light-guiding component that directs response light, of a different wavelength than the stimulation light, to the light detection arrangement 120. In some applications, stimulation light is passed to the cochlear tissue 150 to generate a nonlinear optical response in the cochlear tissue, with light associated with this nonlinear optical response being passed to the light detection arrangement 120 and used to analyze the cochlear tissue.

Figure 2:
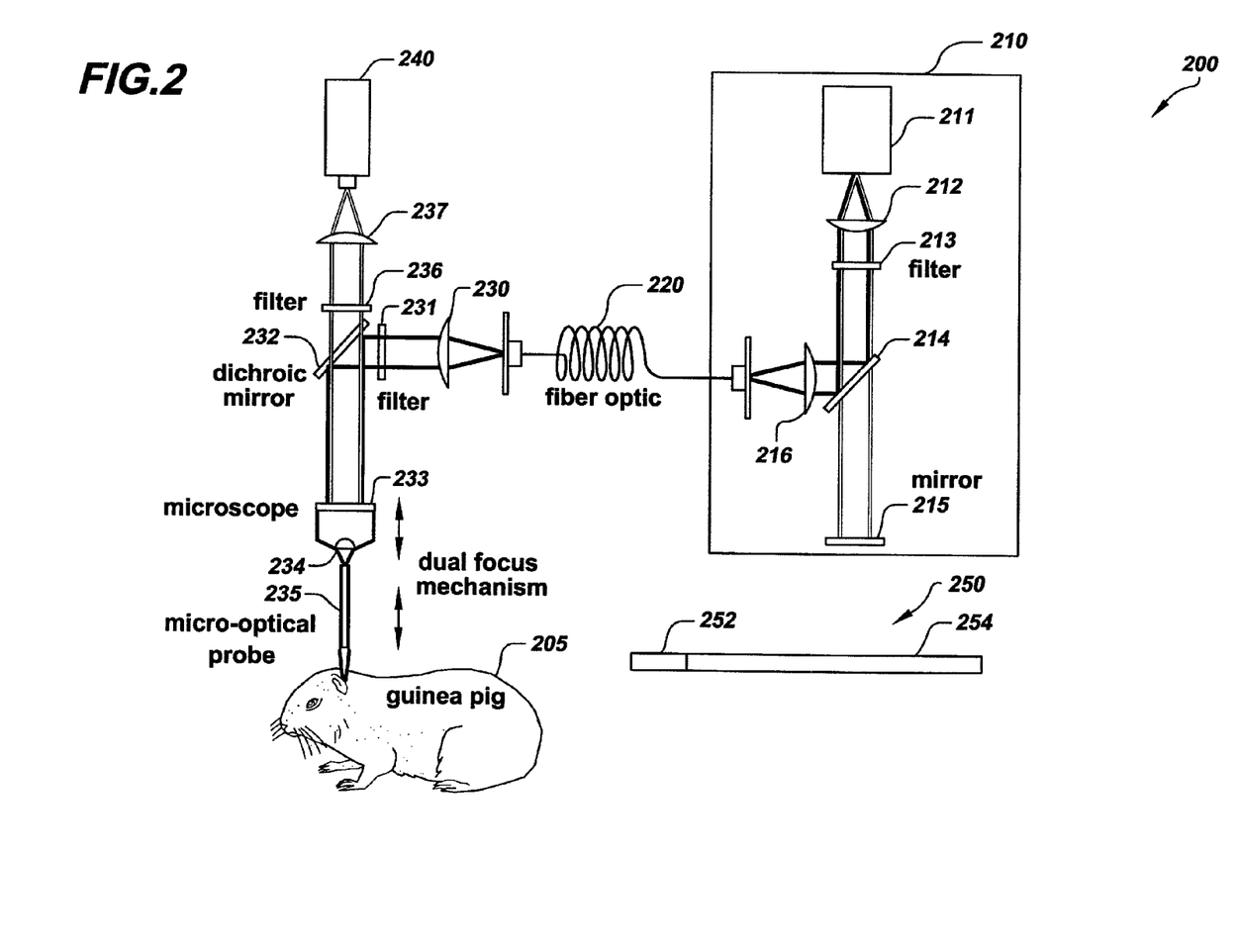
FIG. 2 shows a fluorescence microendoscopy (FME) arrangement 200 for imaging a live being, according to another example embodiment of the present invention.

FIG. 2 shows a FME arrangement 200 for imaging a live being 205 (shown here as a guinea pig by way of example), according to another example embodiment of the present invention. In general, the arrangement 200 includes components that provide light to an endoscope arrangement coupled to a live being, and components that pass light from the live being to a light detector. A light source 211 passes light through a lens 212 and a filter 213 to cold mirror optics (214 and 215) that remove heat from the light (i.e., by splitting infra-red and visible light) before passing the light for use with the imaging of the live being 205. The light is then coupled into a fiber optic conduit 220 using a focusing lens 216.

The fiber optic conduit 220 is coupled near the live being 205 to pass light to a lens 230, filter 231 and dichroic mirror 232 in directing the light to illuminate the live being. From the dichroic mirror 232, the light is passed through microscope optics 233 and 234 to focus the light to a micro-optical probe 235, which is inserted into the live being 205. In some applications, an end of the micro-optical probe 235 is embedded in the live being 205 through a small cochleostomy, or opening of the perilymphatic spaces of the cochlea of the live being.

Light passed into the live being 205 illuminates the live being and/or stimulates tissue in the live being. Light reflected and/or responsive to stimulus from the live being is passed via the micro-optical probe 235, through the optics 233 and 234, through the dichroic mirror 232 and towards a light detector 240, such as a CCD camera or phototube. A filter 236 and lens 237 facilitate the presentation of the light to the light detector 240.

In various applications, some of the components shown in FIG. 2 are coupled and/or combined together, and are located near to or away from the live being 205 (and in some instances, coupled to the live being). For instance, light source components are selectively grouped in an arrangement 210 to include those components providing source light to the fiber optic conduit 220. Similarly, one or more of the components that lie optically between the fiber optic conduit 220 and the live being 205 are coupled, such as with an arrangement similar to that shown in FIG. 3. In addition, the light paths (as shown) are coupled via fiber optic conduit for various applications, such as in the optical path between the dichroic mirror 232 and the light detector 240.

The FME arrangement 200 is used to image cochlear tissue in the live being 205 in one or more of a variety of manners, using one or more approaches to light application and to focusing the light. For instance, some applications are directed to the use of two-photon or one-photon fluorescence microscopy, with the light (photons) directed via the probe 235. For general information regarding microscopy, and for specific information regarding approaches to two-photon or one-photon microscopy that may be implemented in connection with FIG. 2 and one or more example embodiments, reference may be made to one or more of the below-referenced U.S. Patent documents, having Ser. Nos. 11/338,598, 11/334,769 and 11/338,592, as well as to Jung, J. C. and Schnitzer, M. J., *Multiphoton Endoscopy*, Opt Lett 2003; 28: 902-4, all of which are fully incorporated herein by reference. In addition, for more specific information regarding in-vivo imaging approaches involving cochlear tissue, reference may be made to Ashkan Monfared, Nikolas H. Blevins, Eunice L. M. Cheung, Juergen C. Jung, Gerald Popelka, and Mark J. Schnitzer, *In Vivo Imaging of Mammalian Cochlear Blood Flow Using Fluorescence Microendoscopy*, 27:144-152, Otology & Neurotology, Inc. 2006, which is fully incorporated herein by reference.

In connection with one example embodiment of the present invention, one-photon fluorescence microendoscopy is used in connection with the FME arrangement 200, employing compound optics with the micro-optical probe 235, using a GRIN micro-lens doublet including a GRIN objective lens and a much longer GRIN relay lens with a weaker refractive index gradient. One example arrangement of such a doublet lens 250 is shown, having an objective lens 252 and a relay lens 254 with a diameter in the range of between about 350-1000 microns, and adapted for use with the micro-optical probe 235. In some applications, the objective lens 252 exhibits a numerical aperture (NA) near 0.5, for high-resolution imaging at the micron-scale. The doublet lens 250 has a focal distance that is between about 100-800 microns. The objective lens 252 collimates light from a point source in the front focal plane, and the relay lens 254 refocuses the image of the specimen onto the back face of the micro-optical probe 235, from which the image is passed to the light detector 240. The image is selectively magnified, depending upon the application, using a magnification that is between about 4-6×. Resolution in the micro-optical probe 235 is limited with both polychromatic and monochromatic light by the objective lens 252, not by the relay lens 254, with the relay lens providing sufficient length for insertion deep into cochlear tissue, and the corresponding length of the relay lens selected according to this depth.

In various applications, the focus of the micro-optical probe 235 is controlled with two mechanisms, including a compound micro-lens doublet such as the doublet lens 250, and the microscope optics 233 and (objective) 234 to focus an image from the live being 205. The position of the micro-optical probe 235 is adjusted within the live being 205 (e.g., using an approach as shown in and described with FIG. 3), and the lens 234 is positioned relative to the adjusted position of the micro-optical probe. In this regard, once the micro-optical probe 235 is set, image focus is adjusted without necessarily effecting any mechanical movements of the micro-optical probe within the live being 205.

Figure 3:
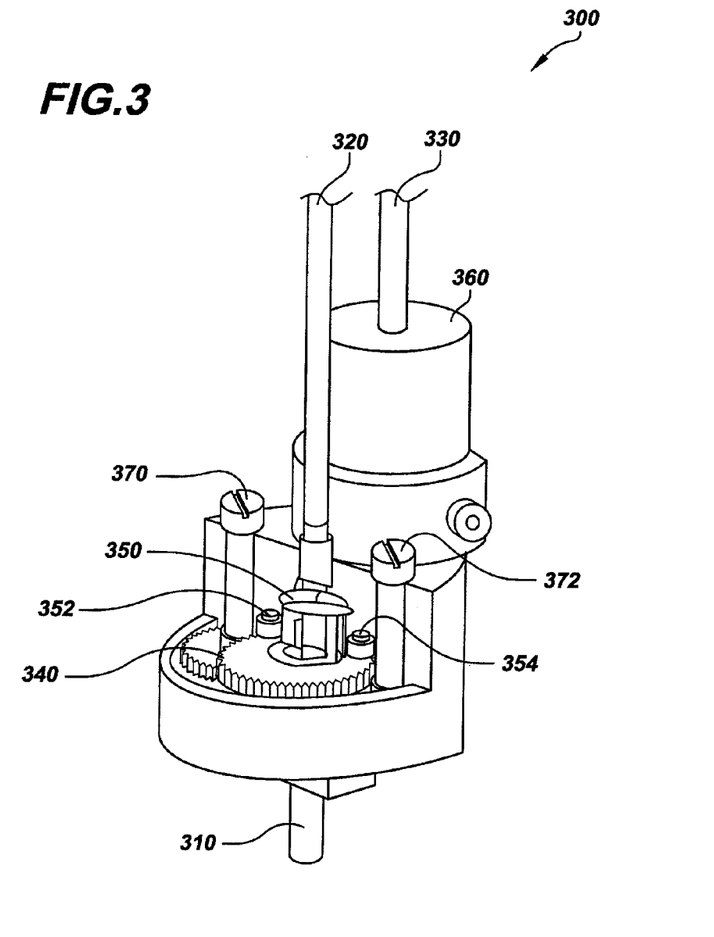
FIG. 3 shows a FME arrangement 300 for use in imaging cochlear tissue, according to another example embodiment of the present invention.

FIG. 3 shows a FME arrangement 300 for use in imaging cochlear tissue, according to another example embodiment of the present invention. The arrangement 300 may, for example, be used in connection with one or more of the various items shown in FIG. 2, and used in the imaging of cochlear tissue of a live being such as a human or guinea pig as discussed by way of example with FIG. 2.

The FME arrangement 300 facilitates the application of a microendoscopic probe 310 to a specimen, for in vivo imaging of cochlear tissue of the specimen. Light is passed to and from the probe 310 using a fiber optic arrangement 320, for respectively illuminating or stimulating the cochlear tissue, and providing image data from the cochlear tissue. For example, relative to FIG. 2, the fiber optic arrangement 320 may be implemented between the micro-optical probe 235 and the objective 234.

A control signal line 330 is coupled to an external input for providing control signals to the FME arrangement 300. In some applications, the control signal line 330 is a wireless connection, with no physical line and with control signals communicated to the arrangement 300 wirelessly.

Gears 340 control the movement of a shuttle 350, using bearings 352 and 354 to facilitate the movement. The shuttle 350 is coupled with the probe 310 such that movement of the shuttle results in movement of the probe. A motor 360 controls the movement of the gears 340 in response to inputs received via the control signal line 330. Support rods 370 and 372 affix the FME arrangement 300 to the live being undergoing analysis.

The fiber optic arrangement 320 includes one or more of a variety of optical fiber arrangements, and in some applications, a bundle of optical fibers. Various example embodiments are directed to the use of optical fibers such as those described in the following U.S. Patent Publications: No. 20050157981 entitled "Miniaturized focusing optical head in particular for endoscope" (to Berier et al.), No. 20050207668 entitled "Method for processing an image acquired through a guide consisting of a plurality of optical fibers" (to Perchant, et al.), No. 20050242298 entitled "Method and equipment for fiber optic high-resolution, in particular confocal, fluorescence imaging" (to Genet, et al.) and No. 20030103262 entitled "Multimodal miniature microscope" (to Richards-Kortum, et al.); and as those described in the following U.S. Pat. Nos. 6,766,184 (Utzinger, et al.) entitled "Methods and apparatus for diagnostic multispectral digital imaging," No. 6,639,674 (Sokolov, et al.) entitled "Methods and apparatus for polarized reflectance spectroscopy," No. 6,571,118 (Utzinger et al.) entitled "Combined fluorescence and reflectance spectroscopy," and No. 5,929,985 (Sandison, et al.) entitled "Multispectral imaging probe," all of which are fully incorporated herein by reference.

The probe 310 is of a diameter and of arrangement that facilitates the insertion of the probe into the cochlea of a living being without necessarily damaging the cochlea. In some applications, the probe 310 has a diameter of about 1000 microns. In other applications, the probe 310 has a diameter of less than about 500 microns, and in still other applications, less than about 350 microns. Generally, the probe 310 has a lens or other optical arrangement near a lower end thereof, for insertion into the cochlea of the patient undergoing analysis. Light is passed into the probe 310 and back from the cochlea via the probe to an external light-detection device.

In connection with various example embodiments of the present invention, a micro-optical probe, such as the probe 235 of FIG. 2 and the probe 310 of FIG. 3, is a microendoscope having lithium doping. In some applications, the micro-optical probe includes a relay having a normal aperture NA of about 0.2, and in other applications, having a NA of about 0.1. The former application with a NA of about 0.2 facilitates a wider field of view and incoupling of excitation light into the endoscope, relative to the latter application with a NA of about 0.1. Such relays are available, for example, from GRINTECH GmbH, Jena, Germany.

Figure 4:
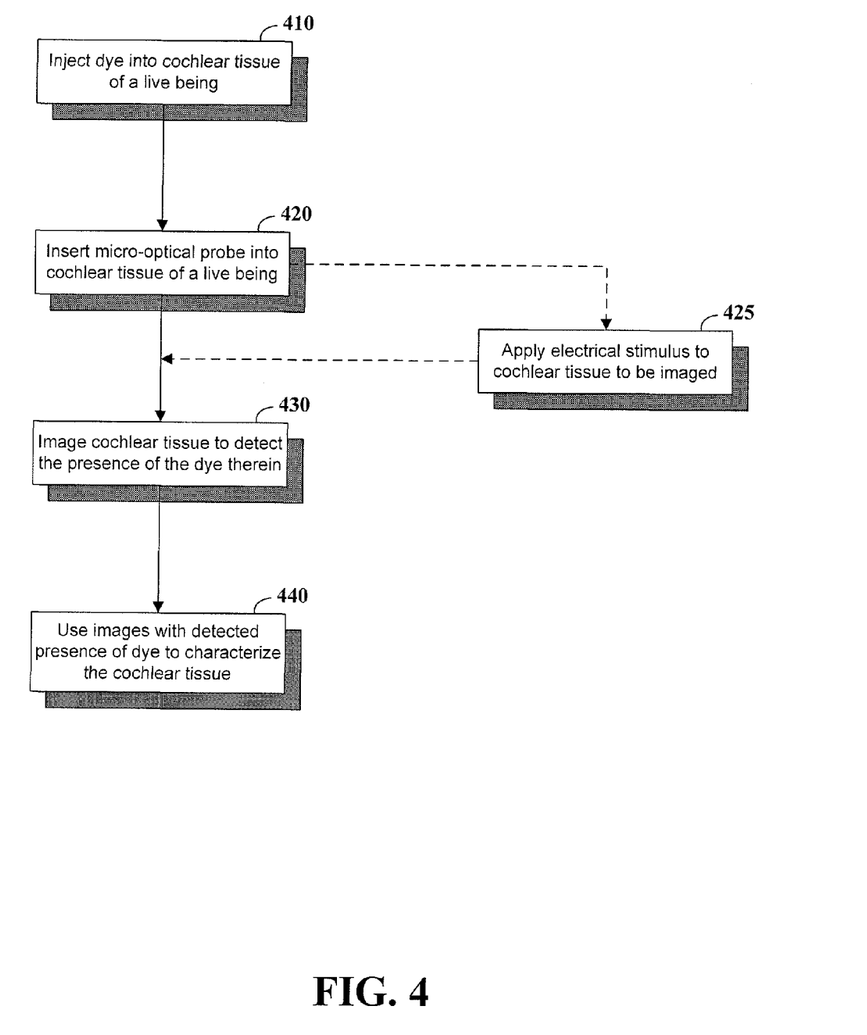
FIG. 4 is a flow diagram showing an approach to analysis of cochlear tissue, according to another example embodiment of the present invention.

FIG. 4 is a flow diagram showing an approach to analysis of cochlear tissue, according to another example embodiment of the present invention. The approach shown in FIG. 4 may, for example, be implemented in connection with one or more of the systems and arrangements shown in the other figures, as well as with a variety of approaches to collecting and analyzing image data from cochlear tissue. At block 410, dye (e.g., fluorescent dye) is injected into cochlear tissue of a live being.

At block 420, a micro-optical probe is inserted into the cochlear tissue, and at block 430, the micro-optical probe is used to image the cochlear tissue to facilitate the detection of the presence of the dye in the tissue. At block 440, the images are used with the detected presence of the dye to characterize the cochlear tissue.

Images obtained at block 430 are used for a variety of purposes, depending upon the application. In one application, the images are used to detect a degree of damage to or recovery of the cochlear tissue. Another application is directed to the use of the images in detecting a response of the tissue to stimulus, such as chemical, physical or electrical stimulus, with the response used, for example, to detect neuronal activity that arises in response to the stimulus. In another application, the images are used to detect the arrangement of the cochlear tissue such as size, position or orientation, which can be used when inserting an implant into the cochlear tissue. In other applications, the images are used to actively guide the insertion of an implant into the cochlear tissue.

In some applications, a voltage-sensitive dye such as RH795, or an ion-sensitive dye (e.g., a dye sensitive to $Ca^{2+}$) is injected at block 410 and used in detecting related cochlear responses. For instance, a dye that changes in fluorescent intensity as a function of the voltage potential in the tissue in which the dye is injected (e.g., the potential of a neuronal membrane) is used in certain applications to facilitate the detection of such changes as related to cochlear function. One such application involves using normalized changes in the intensity of fluorescence intensity to indicate, via linear relation, changes in membrane voltage. The presence and relative degree of neuronal activation is identified via the images obtained at block 440.

In some embodiments, an electrical stimulus is applied at block 425, prior to obtaining images at block 430. In such applications, a voltage-sensitive dye as described above is selectively implemented. In one application, images of the dye collected at block 430 are used to detect the degree and spatial extent of neuronal activation in response to the stimulation at block 440, by relating the response to the distance from the electrode applying the stimulus and to the stimulus intensity. In another application, electrode cross-talk between different stimulus channels are identified and the extent to which each electrode can stimulate a unique population of neurons is mapped. In still another application, cochlear implant arrays with intracochlear electrodes are placed in the scala tympani and images obtained are used to visualize device placement and to map neural excitation created by activation of intracochlear electrodes.

Figure 5:
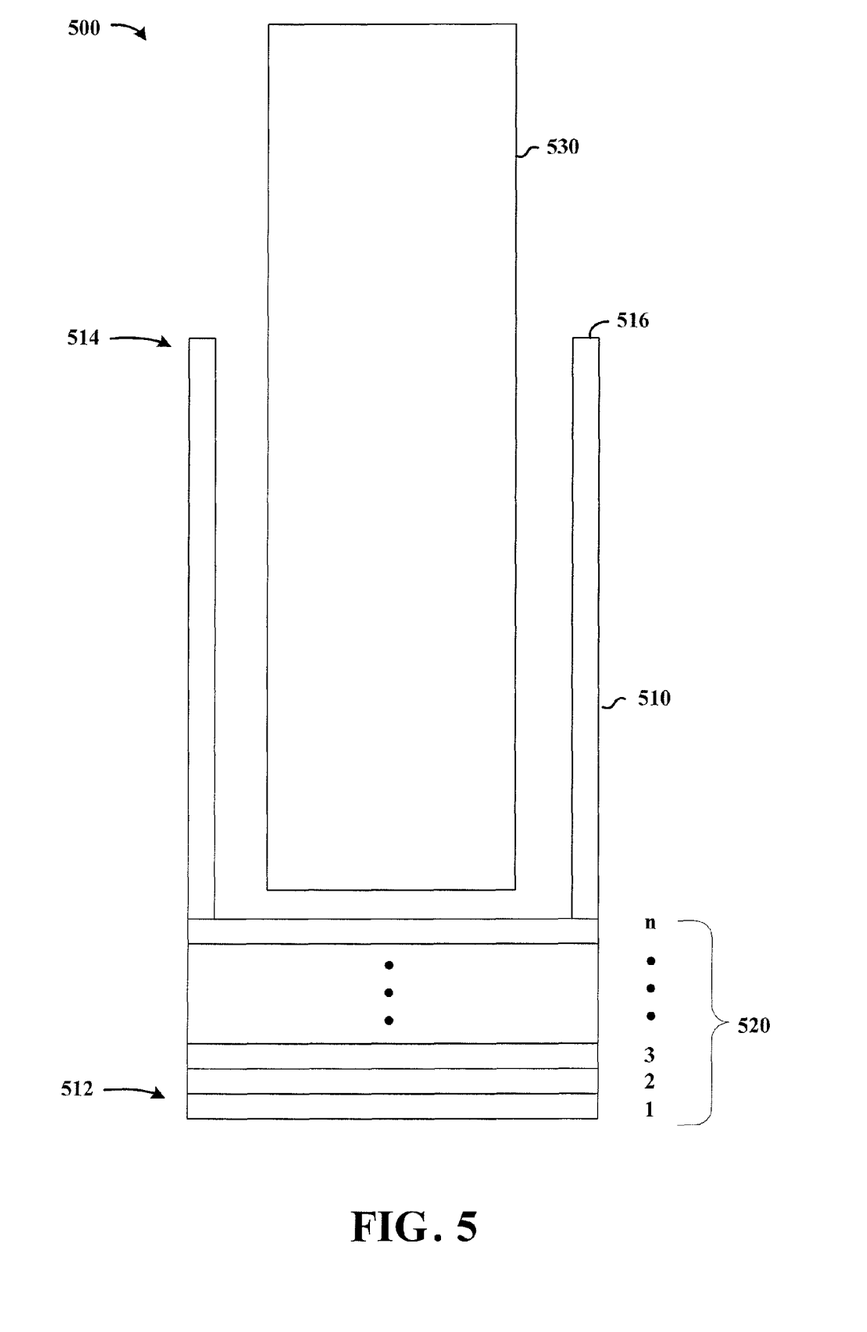
FIG. 5 is a cross-sectional view of a capillary-type arrangement for analyzing a sample, according to another example embodiment of the present invention.

FIG. 5 is a cross-sectional view of a capillary-type arrangement 500 for analyzing a sample, according to another example embodiment of the present invention. The capillary arrangement 500 may, for example, be implemented in connection with the optical analysis system 100 in FIG. 1 to facilitate the passage of light to cochlear tissue 150. The capillary arrangement 500 includes a capillary 510 (e.g., a guiding tube) having a lower closed end 512 and an upper open end 514, with a sidewall 516. Optionally, one or more optical elements 520 are included near the closed end 512 of the capillary 510 for passing light to and from cochlear tissue. The elements 520 may include, for example, a lens-type arrangement that focuses or simply passes light, numbered 1-n by way of example. The capillary 510 is shown in a generally cylindrical shape; however, the shape and corresponding arrangement of the sidewall 516 can be implemented with a variety of shapes for different applications.

In some applications, the optical elements 520 are implemented with a single glass optical element, which is an optical flat of about uniform thickness. The thickness of this single glass optical element is selected to meet particular applications using considerations such as those related to the desire to prevent fracture or damage to the flat and/or to the desire to reduce the optical distance between the analyzed cochlear tissue and an optical probe inserted into the capillary. In one particular application, a glass optical element having a thickness of between about 50 and 500 microns is used to facilitate the aforesaid considerations.

The capillary 510 is adapted for implantation in cochlear tissue of a live being, with the upper open end 514 extending to an accessible location (i.e., outside and/or at a surface of the live being). After implantation, an optical probe 530 such as an endoscope can be inserted into the exposed upper open end 514 of the capillary 510 for passing light via the closed end 512 to the sample in which the capillary 510 is implanted.

The closed end 512 of the capillary 510 generally facilitates the passage of light, and may include one or more of a polished end, glued end, plastic end, ceramic end, glass end and others. In some applications, the closed end 512 includes one or more passageways that are selectively implemented for the passage of fluids to and/or from cochlear tissue in which the capillary 510 is implanted. In some embodiments, the fluid lines are permanently implanted in cochlear tissue along with the capillary, and in other embodiments, the fluid lines are inserted into the specimen (and reinserted as appropriate for subsequent analysis) via specific routes in the capillary.

In one application, the capillary 510 has a generally cylindrical shape, with inner and outer diameters (as defined by the sidewall 516) respectively about 1.4 mm and 1.6 mm. A generally round light-passing piece is glued at the lower end 512 of the capillary 510 and the arrangement is cured. A fiber grinder is used to polish the capillary, in particular the light-passing piece and the glued lower end 512 of the capillary 510.

In some implementations, the capillary 510 is adapted for implantation into the cochlear tissue of a live being to facilitate optical analysis over the course of time, with the capillary left implanted in the being during times in-between instances of optical analysis. For example, the capillary can be implanted in cochlear tissue such that the closed end thereof facilitates the passage of light to and from target areas of the tissue. With this approach, the upper open end 514 of the capillary 510 is available for the insertion of a probe thereto, facilitating access into the live being with the probe from a relative external position. In some instances, the open end 514 of the capillary 510 is accessible via outer tissue of the being, such as via the skin or skull tissue of the being. In other instances, the open end 514 of the capillary 510 is inside of the live being, but accessible by a probe (e.g., where the capillary is implanted in a region accessible via a blood vessel or via non-invasive or invasive type approaches).

Once implanted, the capillary 510 is used to selectively optically access cochlear tissue near the capillary over the course of hours, days, weeks, months or more. In this regard, the study of a live being over time is facilitated, such as for the reaction of the live being to a particular treatment. For example, damaged cochlear tissue can be imaged and monitored via the capillary over time to detect recovery from the damage.

In certain applications, additional functional components such as fluid lines, electrodes and others are implemented with the capillary 510. These components may be implemented, for example, to stimulate or otherwise affect the cochlear tissue adjacent to the capillary 510, such as by electrically stimulating the tissue or by supplying drugs, dyes or other fluids to the tissue. These components can also be used to monitor the tissue, such as by facilitating electrophysiological recordings or fluidic sampling of specimens to be analyzed using genetic, biochemical, cytometric or other approaches.

In some example embodiments involving the application of electrical stimulus to cochlear tissue, one or more electrodes are located at an implanted portion of the capillary 510 to facilitate the passage of the electrical stimulus into the cochlear tissue. In another implementation, electrodes at an implanted portion of the capillary 510 are used to facilitate in vivo recordings of neuronal activity at the imaging field. In some embodiments, electrodes are permanently implanted in the cochlear tissue along with the capillary arrangement 500, and in other embodiments, the electrodes are inserted into the specimen (and reinserted for subsequent analysis) via specific routes in the capillary. These approaches to electrical and chemical analysis may be implemented, for example, in connection with the approaches described with FIG. 4.

The one or more optical elements 520 include one or more of a variety of light-passing arrangements. In one implementation, the one or more optical elements 520 include gradient refractive index (GRIN) optics such as a GRIN lens or GRIN lens array that facilitates the collimation of light. In another application, the optical elements 520 include a variable focal length lens, adaptable for focusing upon subjects at different focal depths. In other applications, the optical elements include a liquid lens.

In another example embodiment of the present invention, a capillary such as the capillary 510, or a similar capillary without a closed end, is adapted to facilitate the placement of a rigid endoscopic probe for cochlear imaging. Generally, such an approach facilitates the insertion of a relatively thin (e.g., 500 μm to 1 mm diameter) microendoscope probe, such as the probe 235 of FIG. 2 or the probe 310 of FIG. 3, into relatively small (e.g., 2 mm) holes separated by a relatively large distance (e.g., 1 cm or more) to reach the cochlea of a live being. In addition, this approach facilitates the insertion of such a probe while generally preserving sensitive and surrounding anatomical structures, such as the facial nerve and blood supply.

The capillary discussed above is implemented in one or more of a variety of manners. In some applications, the capillary is a glass capillary guide tube that includes a cut glass capillary and at least one reflective metal washer epoxied about perpendicularly to the central axis of the capillary. The inner diameter of the guide tube is chosen to match the diameter of the endoscope. A small (e.g., less than about 1 mm) hole or cochleostomy is drilled in the cochlea using a surgical microscope, and a capillary guide tube is placed so that the cochlea is sighted through the central bore of the guide tube to allow access for imaging. The tube is then affixed onto part of the outer skull using, for example, bone wax or dental acrylic. The microendoscope probe is oriented by eye through the guide tube using the surgical microscope, by a weak laser beam bounced off the metal washer to orient endoscope placement, or another appropriate approach.

Figure 6A:
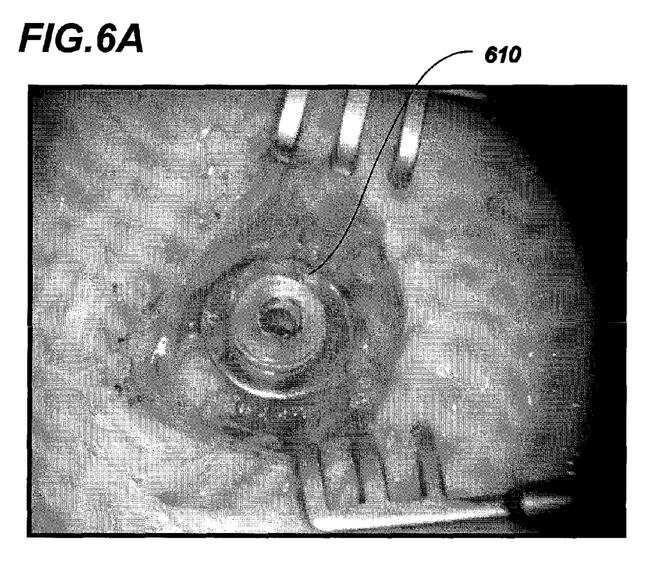
FIG. 6A shows a capillary arrangement and approach, according to another example embodiment of the present invention.

FIG. 6A shows a capillary arrangement 610 and approach, according to another example embodiment of the present invention. The capillary arrangement 610 is inserted into a subject for imaging of cochlear tissue and may, for example, be implemented in connection with the approach described in the previous paragraphs.

Figure 6B:
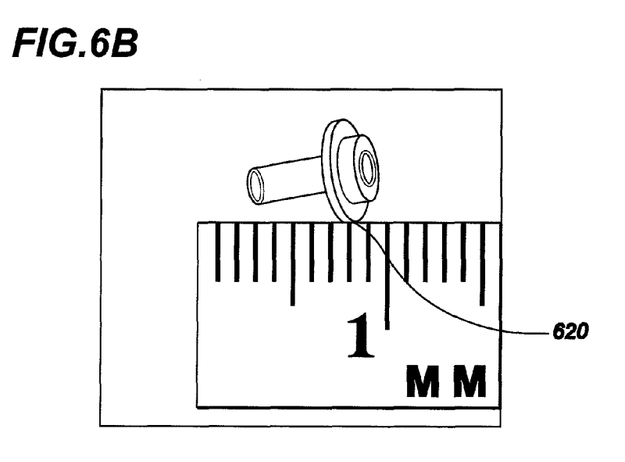
FIG. 6B shows a capillary arrangement and approach, according to another example embodiment of the present invention.

FIG. 6B shows a capillary 620 including a cut glass piece as may be implemented as shown with FIG. 6A, according to another example embodiment of the present invention. The capillary 620 is shown, by way of example, next to a scale; however, a variety of sizes and arrangements of the capillary 620, as may be implemented, for example, with the capillary 610 in FIG. 6A, are used in connection with one or more example embodiments.

For general information regarding capillary analysis approaches, and for specific information regarding approaches to cochlear tissue analysis with a capillary, and in particular with fluid and/or electrical analysis approaches, reference may be made to U.S. patent application Ser. No. 11/334,769 as referenced below.

According to another example embodiment of the present invention, fluorescence microendoscopy is implemented to visualize transduction inside mammalian cochlea in vivo, to observe how this transduction is disrupted in a noise-damaged subject, and to image the cochlea as it recovers over time. These approaches may be implemented, for example, in connection with one or more of the figures discussed above. In these embodiments, mechanosensitive hair cells are observed in the inner ear using fluorescence microendoscopy and fluorescent labeling of hair cells with a dye that reveals cell morphology and reports intact mechanotransduction.

In one implementation, the basal turn of the cochlea of a live being is accessed through the mastoid bulla. A small cochleostomy is performed and a dye is injected into the scala media. A microendoscope is inserted through the scala tympani to examine the Organ of Corti, and fluorescence images of stereocilia are obtained using a microendoscope.

In some embodiments, functional hair cells are visualized with a fluorescent dye that preferentially labels transducing hair cells. In one implementation, a styryl pyridinium dye called FM1-43 is used in such an analysis approach. The FM1-43 rapidly partitions into the outer leaflet of cell membranes, but diffuses out rapidly. This dye rapidly enters hair cells of the inner ear through mechanically-gated transduction channels of the hair cells, and is trapped inside for days. The FM1-43 sequestered within hair cells partitions into inner membranes and brightly labels the stereocilia of the hair cell. Using this characteristic, structural damage to the bundle is observed to visualize morphological and functional changes to hair cells in the cochlea due to acoustic overstimulation.

In some applications, the cochlea on one side are imaged directly after noise damage is induced in subjects (e.g., guinea pigs), with cochlea on an opposite side imaged after several hours to analyze any hearing recovery. Images showing a reduction of fluorescence dye entry into damaged cells are used to identify and/or characterize the damaged cells (i.e., acoustic trauma causes the breaking of mechanical linkages to transduction channels). For instance, where breakage of the tip links alone is responsible for temporary threshold shift (TTS) hearing loss, the hair cells of a TTS subject imaged directly after noise exposure show decreased dye uptake near the site corresponding to the damaging sound frequency. However, sterocilia bundles will remain morphologically intact, and dye uptake should return to normal once there has been sufficient time allowed for the tip link to regenerate.

Where a subject has experienced more permanent acoustic trauma (i.e., severe damage to the hearing organ), images indicate decreased dye uptake in hair cells, increasingly disarrayed and broken stereocilia, and damage to hair cells and perhaps surrounding structures.

In another example embodiment of the present invention, the effectiveness of pharmacological treatment or genetherapy upon hearing loss is analyzed using an in-vivo optical analysis approach as discussed herein. In some applications, such an approach is implemented to assess the cause of hearing loss in humans, and for diagnostics preceding cochlear implantation.

In the above example embodiments as well as others herein, a variety of imaging approaches employing microendoscopes and/or other devices are implemented to facilitate the analysis of cochlear tissue. For general information regarding imaging approaches, and for specific examples of imaging arrangements and approaches that may be implemented in connection with one or more example embodiments of the present invention, reference may be made to the following U.S. Patent Documents as referenced above: Ser. No. 11/338,598, entitled "LIVE BEING OPTICAL ANALYSIS SYSTEM AND APPROACH"; Ser. No. 11/334,769, entitled "OPTICAL ANALYSIS SYSTEM AND APPROACH THEREFOR"; and Ser. No. 11/338,592 (U.S. Pat. No. 7,307,774), entitled "MICRO-OPTICAL ANALYSIS SYSTEM AND APPROACH THEREFOR," all of which are fully incorporated herein by reference.

Various example embodiments are also directed to one or more of the approaches described in the underlying provisional-application Appendices, alone and/or in combination with other example embodiments discussed above and/or in the Appendices, which are incorporated by reference.

While the present invention has been described with reference to several particular example embodiments, those skilled in the art will recognize that many changes, including those discussed in the preceding paragraph, may be made thereto without departing from the spirit and scope of the present invention.

What is claimed is:

1. A method for in-vivo viewing of cochlear tissue of a live being, the method comprising:
    inserting a lower distal end of a micro-optical probe into cochlear tissue of the live being;
    directing light to the cochlear tissue via the micro-optical probe;
    passing light from the cochlear tissue, via the micro-optical probe, to an external imaging arrangement; and
    at the external imaging arrangement, using the light passed from the cochlear tissue to optically image fluid of the live being in a field of view with the micro-optical probe inserted into the cochlear tissue, and thereby indicating a condition of functionality of sensory receptor cells of the cochlear tissue.

2. The method of claim 1, wherein using the light passed from the cochlear tissue to optically image fluid of the live being includes optically imaging blood flow in the cochlear tissue.

3. The method of claim 2, wherein optically imaging blood flow includes optically imaging the flow of individual blood cells, further including using the imaged flow of individual blood cells to determine a velocity of the flow of the individual blood cells in an individual blood vessel, thereby indicating a condition of functionality of the sensory receptor cells.

4. The method of claim 1, further including determining a condition of auditory function of the live being with the optically-imaged fluid of the live being.

5. The method of claim 1, further including identifying a portion of the cochlear tissue exhibiting auditory malfunction as a function of the imaged fluid and implanting a cochlear prosthesis into the live being to mitigate the auditory malfunction.

6. The method of claim 5, further including using the light passed from the cochlear tissue to guide the implant of the cochlear prosthesis into the live being.

7. The method of claim 1, further including using the light passed from the cochlear tissue to guide the implant of a cochlear prosthesis into the live being.

8. The method of claim 1, wherein directing light to the cochlear tissue via the micro-optical probe, passing light from the cochlear tissue, and using the light passed from the cochlear tissue to optically image fluid of the live being includes optically imaging the fluid of the live being via one-photon fluorescence microscopy.

9. The method of claim 1, further including introducing a fluorescent dye to the live being, wherein using light passed from the cochlear tissue to optically image fluid of the live being includes using a fluorescent response of the dye.

10. The method of claim 9, wherein introducing a fluorescent dye includes introducing a voltage-sensitive dye that changes in fluorescent intensity as a function of the voltage potential in the tissue in which the dye is injected, further including detecting the intensity of light passing from the cochlear tissue to detect a voltage potential of the cochlear tissue.

11. The method of claim 9, wherein introducing a fluorescent dye includes introducing a chemical-sensitive dye that changes in fluorescence as a function of chemicals in the tissue in which the dye is injected, and wherein using a fluorescent response of the dye includes detecting a chemical in the cochlear tissue with the fluorescent response.

12. The method of claim 1, wherein inserting a lower distal end of a micro-optical probe into cochlear tissue of the live being includes inserting the probe in a manner that does not substantially alter the cochlear tissue, whereby auditory function of the live being is maintained in a substantially unaffected manner, upon removal of the probe.

13. The method of claim 1, wherein inserting a lower distal end of a micro-optical probe into cochlear tissue includes inserting a micro-optical probe having a doublet lens.

14. The method of claim 13, further including manipulating an objective lens, relative to a doublet lens, to focus to a selected depth into the cochlear tissue, the objective lens being external to the live being.

15. The method of claim 1, further including using the optical image of the fluid to detect damaged cochlear tissue, and using the micro-optical probe to guide the manipulation of a portion of the cochlear tissue.

16. The method of claim 1, further including using the optical image of the fluid to detect damaged cochlear tissue, and using the micro-optical probe to guide the removal of a portion of the cochlear tissue.

17. The method of claim 1, further including electrically stimulating the cochlear tissue to generate cochlear neural activity in a manner that mimics nonlinear mechanisms of cochlear transduction.

18. The method of claim 1, wherein inserting a lower distal end of a micro-optical probe into cochlear tissue of the live being includes embedding the lower distal end of the micro-optical probe in the live being through a small opening of the perilymphatic spaces of the cochlea of the live being.

19. The method of claim 1, prior to inserting a lower distal end of a micro-optical probe into cochlear tissue of the live being, inserting a capillary into the cochlear tissue of the live being, wherein inserting a lower distal end of a micro-optical probe into cochlear tissue of the live being includes inserting the lower distal end of the micro-optical probe into the capillary.

20. The method of claim 1, wherein inserting a lower distal end of a micro-optical probe into cochlear tissue of the live being includes inserting the probe while maintaining auditory function of the cochlear tissue.

21. A method for in-vivo analysis of cochlear tissue of a live being, the method comprising:
    introducing a fluorescent dye to the blood of the live being and labeling blood cells with the dye;
    inserting a lower distal end of a micro-optical probe into cochlear tissue of the live being;
    directing light to blood in the cochlear tissue via the micro-optical probe and causing fluorescent emissions from blood cells labeled with the fluorescent dye;
    passing the fluorescent emissions from the cochlear tissue, via the micro-optical probe, to an external imaging arrangement;
    at the external imaging arrangement, using the passed fluorescent emissions to obtain images of individual blood cells that characterize blood flow in the cochlear tissue of the live being; and
    using the imaged blood flow to determine a condition of auditory function of the cochlear tissue.

22. The method of claim 21, wherein directing light to blood in the cochlear tissue includes causing a one-photon emission.

23. The method of claim 22, wherein directing light to blood in the cochlear tissue includes causing a two-photon emission.

24. An arrangement for in-vivo viewing of cochlear tissue of a live being using a capillary inserted into the cochlear tissue, the arrangement comprising:
    a micro-optical probe configured and arranged for insertion into the cochlear tissue of the live being via the capillary and to direct light to the cochlear tissue and to pass light, from the cochlear tissue to an imaging arrangement, to indicate a condition of functionality of sensory receptor cells of the cochlear tissue; and
    the imaging arrangement being configured and arranged to receive and use the light passed from the cochlear tissue to optically image fluid of the live being in a field of view with the micro-optical probe inserted into the cochlear tissue to indicate the condition of functionality of sensory receptor cells of the cochlear tissue.

25. The arrangement of claim 24, further including a light direction arrangement configured to direct light to the cochlear tissue via the micro-optical probe, and to pass light, received from the cochlear tissue via the micro-optical probe, to the external imaging arrangement.

26. The arrangement of claim 24, wherein the micro-optical probe is configured and arranged to direct stimulation light into the live being and to pass a fluorescent response to the stimulation, from the cochlear tissue to an external imaging arrangement.

27. The arrangement of claim 24, wherein the micro-optical probe is of a diameter and length to facilitate its insertion into cochlear tissue without substantially affecting auditory function of the live being.

28. A method for in-vivo cochlear sensory receptor cell analysis, the method comprising:
    inserting a lower distal end of a micro-optical probe into cochlear tissue of a live being to direct light to the cochlear tissue and to pass light from the cochlear tissue to an external imaging arrangement;
    using active transduction channels in hair cells of the cochlear tissue to flow die to sensory receptor cells in the cochlear tissue and label functioning sensory receptor cells;
    at the external imaging arrangement, using the light passed from the cochlear tissue to optically image fluid in sensory receptor cells of the cochlear tissue in a field of view with the micro-optical probe inserted into the cochlear tissue; and
    providing an indication of a condition of functionality of the sensory receptor cells in response to the image.

* * * * *